(12) United States Patent
Matsumoto

(10) Patent No.: US 7,766,819 B2
(45) Date of Patent: Aug. 3, 2010

(54) ENDOSCOPE AND ENDOSCOPE TIP FORMING MEMBER

(75) Inventor: Kazutaka Matsumoto, Fuchu (JP)

(73) Assignee: Olympus Corporation (JP)

( * ) Notice: Subject to any disclaimer, the term of this patent is extended or adjusted under 35 U.S.C. 154(b) by 201 days.

(21) Appl. No.: 11/289,954

(22) Filed: Nov. 30, 2005

(65) Prior Publication Data

US 2006/0111612 A1    May 25, 2006

Related U.S. Application Data

(63) Continuation of application No. PCT/JP2004/007780, filed on May 28, 2004.

(30) Foreign Application Priority Data

May 30, 2003    (JP)    ............................. 2003-155629

(51) Int. Cl.
A61B 1/00    (2006.01)
(52) U.S. Cl. .................... 600/129; 600/128; 600/146
(58) Field of Classification Search .......... 600/127–129, 600/146, 104, 114, 121, 164, 176
See application file for complete search history.

(56) References Cited

U.S. PATENT DOCUMENTS

| | | | | |
|---|---|---|---|---|
| 4,753,224 A * | 6/1988 | Tojo | ............................. | 600/129 |
| 4,911,148 A | 3/1990 | Sosnowski et al. | | |
| 5,383,849 A * | 1/1995 | Johlin, Jr. | ..................... | 604/500 |
| 5,662,588 A * | 9/1997 | Iida | ............................ | 600/127 |
| 5,681,262 A * | 10/1997 | Isse | ............................ | 600/127 |
| 6,432,044 B1 * | 8/2002 | Lunsford et al. | ............. | 600/129 |
| 6,656,112 B2 * | 12/2003 | Miyanaga | ..................... | 600/129 |
| 2002/0032367 A1 * | 3/2002 | Akiba | ........................ | 600/127 |
| 2002/0183591 A1 * | 12/2002 | Matsuura et al. | ............ | 600/127 |
| 2002/0188177 A1 * | 12/2002 | Miyanaga | ..................... | 600/179 |
| 2002/0193662 A1 * | 12/2002 | Belson | ........................ | 600/117 |
| 2003/0032860 A1 * | 2/2003 | Avni et al. | .................. | 600/121 |
| 2003/0088154 A1 * | 5/2003 | Ishibiki et al. | .............. | 600/127 |

(Continued)

FOREIGN PATENT DOCUMENTS

JP    08-252211    10/1996

(Continued)

OTHER PUBLICATIONS

Untranslated Office Action issued by Japanese Patent Office on Mar. 14, 2006 in connection with corresponding Japanese patent application No. 2003-155629.

(Continued)

*Primary Examiner*—John P Leubecker
*Assistant Examiner*—Victoria W Chen
(74) *Attorney, Agent, or Firm*—Ostrolenk Faber LLP

(57) ABSTRACT

An endoscope including an elongated insertion section configured to be inserted into a lumen of a subject's body from the distal end side thereof, a tip forming portion which forms a distal end portion of the insertion section, and a bending section which is formed on the insertion section and is bent to move the tip forming portion in a given direction. A slope portion is formed on the given-direction side of the tip forming portion. The slope portion is located so that the tip forming portion is tapered from the rear end side toward the distal end side and abuts against an inner wall of the lumen.

4 Claims, 8 Drawing Sheets

U.S. PATENT DOCUMENTS

2004/0242963 A1* 12/2004 Matsumoto et al. ......... 600/127
2005/0137499 A1*  6/2005 Sheets et al. ................ 600/562
2007/0219466 A1*  9/2007 Tremulis et al. ............ 600/585

FOREIGN PATENT DOCUMENTS

| JP | 10-309259   | 11/1998 |
| -- | ----------- | ------- |
| JP | 11-056753   | 3/1999  |
| JP | 2000-271064 | 10/2000 |
| JP | 2003-33315  | 2/2003  |

OTHER PUBLICATIONS

English translation of Office Action issued by Japanese Patent Office on Mar. 14, 2006 in connection with corresponding Japanese patent application No. 2003-155629.

Untranslated Office Action issued by Japanese Patent Office on Nov. 29, 2005 in in connection with corresponding Japanese application No. 2003-155629.

English translation of Japanese Office Action dated Nov. 29, 2005 issued in connection with corresponding Japanese application No. 2003-155629.

Chinese Office Action mailed Jul. 17, 2009 in corresponding Chinese Patent Application No. 200480015081.7 (with English language translation).

Letter from Chinese associate dated Aug. 12, 2009 forwarding the Chinese Office Action dated Jul. 17, 2009 to Japanese associate. Chinese associate's letter dated Aug. 12, 2009 was date stamped received by Japanese associate on Aug. 14, 2009 (partial English language translation).

International Search Report for PCT/JP2004/007780 dated Jun. 17, 2004.

* cited by examiner

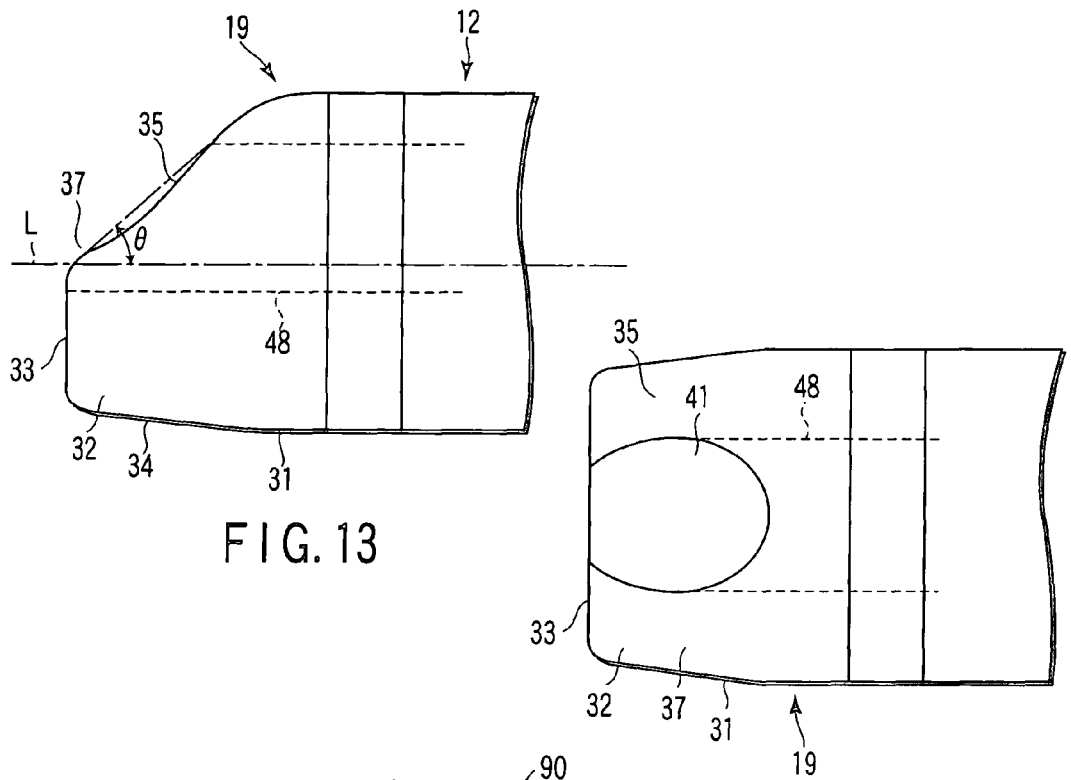
FIG. 13
FIG. 14
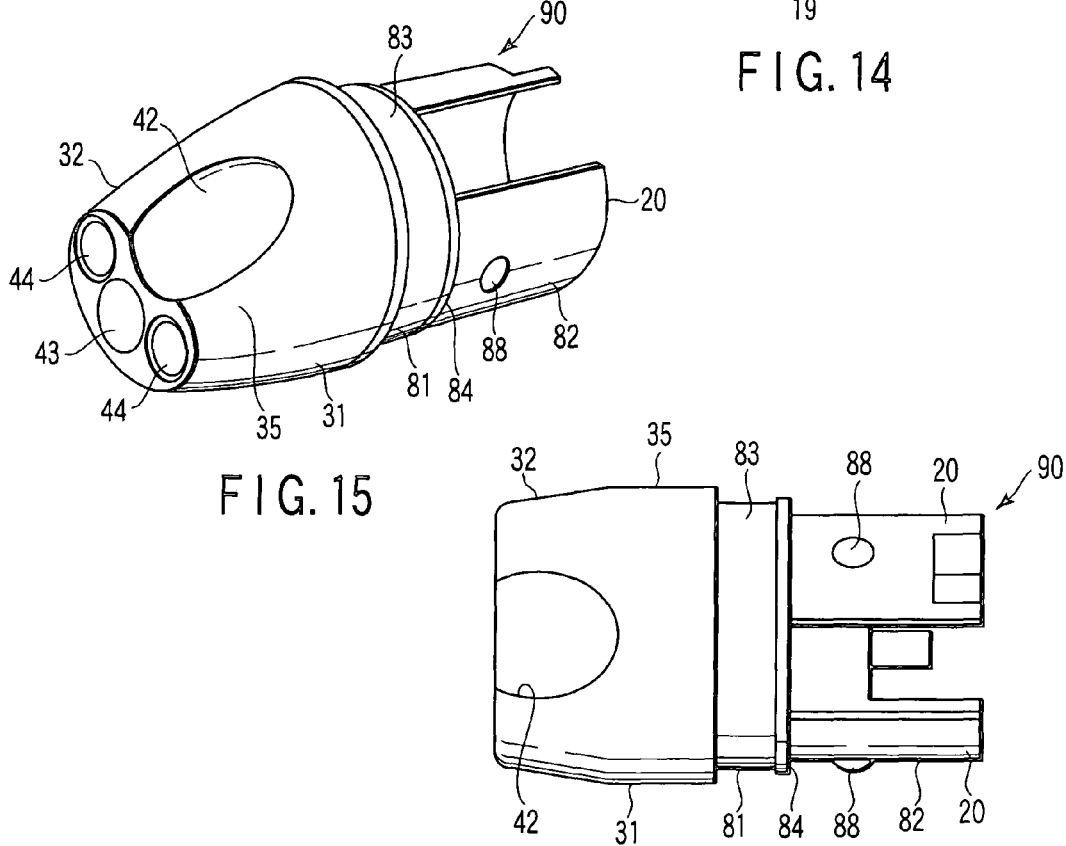
FIG. 15
FIG. 16

ENDOSCOPE AND ENDOSCOPE TIP FORMING MEMBER

CROSS REFERENCE TO RELATED APPLICATIONS

This is a Continuation Application of PCT Application No. PCT/JP2004/007780, filed May 28, 2004, which was published under PCT Article 21(2) in Japanese.

This application is based upon and claims the benefit of priority from prior Japanese Patent Application No. 2003-155629, filed May 30, 2003, the entire contents of which are incorporated herein by reference.

BACKGROUND OF THE INVENTION

1. Field of the Invention

The present invention relates to a medical endoscope configured to be inserted into a lumen of a subject's body to observe the subject's body.

2. Description of the Related Art

While various techniques are conventionally used to insert an endoscope into a lumen of a subject's body, a technique to insert the endoscope into an occluded lumen is very difficult. In inserting the endoscope into the occluded lumen, moreover, the inner wall of the lumen is rubbed by corners of the distal end portion of an insertion section, so that pain is inflicted on the patient.

An endoscope for urinary organs described in Jpn. Pat. Appln. KOKAI Publication No. 2000-271064 is an example of an endoscope that can be suitably inserted into such an occluded lumen. The cross section of an insertion section of this endoscope has the shape of an ellipse that agrees with the cross section of a urethra in the shape of a teardrop that is vertically long and laterally narrow. In inserting the insertion section into the urethra, therefore, the urethra is expected to be laterally extended only a little. Thus, compression of the left and right inner walls of the urethra by the insertion section can be reduced, and the ease of insertion of the insertion section is improved.

An endoscope described in Jpn. Pat. Appln. KOKAI Publication No. 10-309259 is another example of an endoscope that can be suitably inserted into an occluded lumen. This endoscope is configured to be inserted into a large intestine through the anus. The anus has the shape of an ellipse that is flattened between buttocks. In order to facilitate the insertion into the flattened occluded anus, round chamfer portions are formed by chamfering corners at the opposite edge portions of the distal end face of the insertion section according to the shape of the anus. In consequence, the ease of insertion of the insertion section into the anus is improved.

Incidentally, as shown in FIG. 21, the urethra 1 of a male person extends from the external urethral orifice 2 to the urinary bladder 4 through the urethral sphincter 3 and the prostate 6. The urethra 1 horizontally extends straight from the external urethral orifice 2 to a part just short of the urethral sphincter 3 and bends upward at this part. Further, the urethra 1 upwardly extends straight from this bent part 5 to the urinary bladder 4. Thus, the urethra 1 sharply bends at the bent part 5.

Since the urethral sphincter 3 fulfills a throttle function to close up the urethra 1, moreover, the urethra 1 is narrowed near the urethral sphincter 3. In the case of a patient whose prostate 6 is starting to hypertrophy, furthermore, the urethra 1 is narrowed near the prostate 6. Thus, the urethra 1 tends to be occluded in a region that extends from the bent part 5 to the urinary bladder 4.

BRIEF SUMMARY OF THE INVENTION

A preferred aspect of the present invention is an endoscope comprising an elongated insertion section configured to be inserted into a lumen of a subject's body from the distal end side thereof, a tip forming portion which forms a distal end portion of the insertion section, a bending section which is formed on the insertion section and is bent to move the tip forming portion in a given direction, and a slope portion formed on the given-direction side of the tip forming portion, the slope portion being located so that the tip forming portion is tapered from the rear end side toward the distal end side and configured to abut against an inner wall of the lumen.

A preferred aspect of the present invention is an endoscope tip forming member comprising a body section, a slope portion formed on the body section so that the body section is tapered from one end side toward the other end side and configured to abut against an inner wall of a lumen of a subject's body, and a connecting portion provided on the one end side of the body section and connected to a distal end portion of a bending section of an endoscope, the connecting portion being connected to the bending section so that the slope portion is located on the side of that direction in which the distal end portion is moved as the bending section bends.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 13 is a side view showing the tip forming portion of the endoscope of the same embodiment;

FIG. 14 is a top view showing the tip forming portion of the endoscope of the same embodiment;

FIG. 15 is a perspective view showing a tip forming member of the endoscope of the same embodiment;

FIG. 16 is a top view showing the tip forming member of the endoscope of the same embodiment;

DETAILED DESCRIPTION OF THE INVENTION

An embodiment of the present invention will now be described with reference to the drawings. An endoscope of the present embodiment is a forward-viewing-type flexible endoscope for urinary organs configured to be inserted into the urethra. Alternatively, the present invention may be applied to an endoscope for a uterus, a lower digestive organ, etc.

Figure 1:
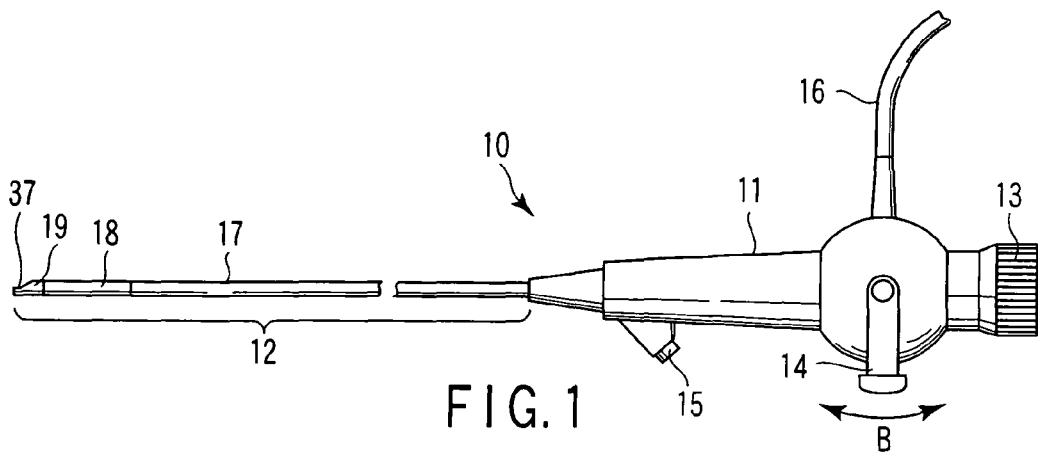
FIG. 1 is a side view of an endoscope according to one embodiment of the present invention.

FIG. 1 shows a general outline of an endoscope 10 of the present embodiment. The endoscope 10 has a flexible insertion section 12 that is inserted into a lumen of a subject's body. The insertion section 12 is formed by successively coupling together a tip forming portion 19, a bending section 18, and a flexible tube section 17 from the distal end side. The bending section 18 can be bent by a bending mechanism, which will be mentioned later. The flexible tube section 17, which has flexibility, is configured to curve in response to an external force applied to it and be restored when the external force is removed.

A hand control section 11 connects with the proximal end portion of the insertion section 12. The hand control section 11 is provided with a bending operation lever 14 for bending the bending section 18. Further, the hand control section 11 is provided with an eyepiece section 13 and a channel connector 15 and is coupled with a light guide cable 16. A connector (not shown) is provided on the extreme end portion of the light guide cable 16. This connector is connected to an endoscopic light source unit (not shown) when the endoscope 10 is in use.

In the present embodiment, the bending section 18 can bend only in two given opposite directions which extend substantially at right angles to the longitudinal axis of the endoscope 10. This bending direction will be referred to as the vertical direction. Further, a direction that is perpendicular to the longitudinal axis of the endoscope 10 and the vertical direction will be referred to as the lateral direction. When the bending operation lever 14 of the hand control section 11 is rocked (see arrow B in FIG. 1), the bending section 18 is made to be bent only in the vertical direction, thereby moving the tip forming portion 19 in a given direction.

Figure 2:
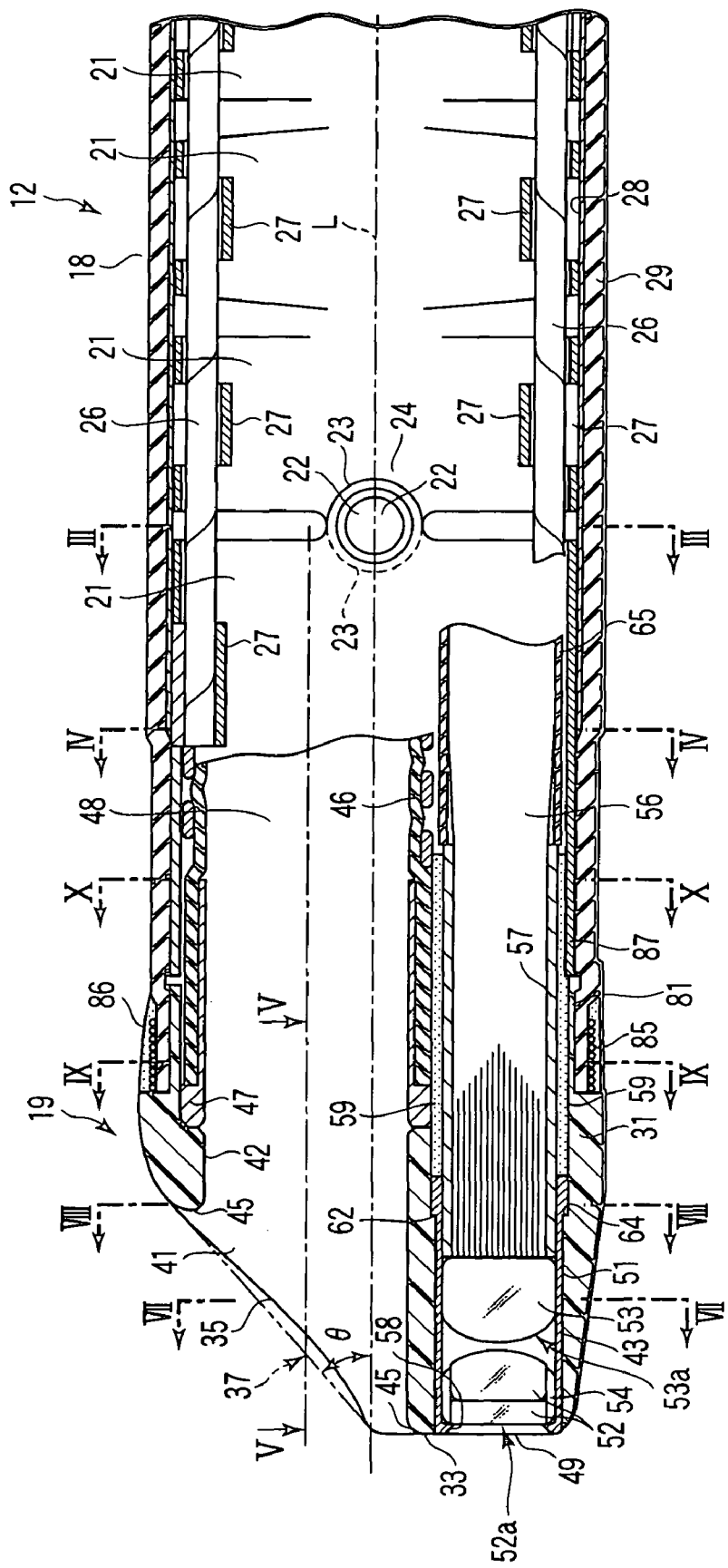
FIG. 2 is a longitudinal sectional view showing a tip forming portion and a bending section of the endoscope of the same embodiment.

The following is a detailed description of a configuration of the bending section 18. As shown in FIG. 2, the bending section 18 has a plurality of bending pieces 21 that are arranged side by side along a central axis L (longitudinal axis) of the insertion section 12. The adjacent bending pieces 21 are connected to one another so as to be rotatable in the vertical direction and nonrotatable in the lateral direction.

Figure 3:
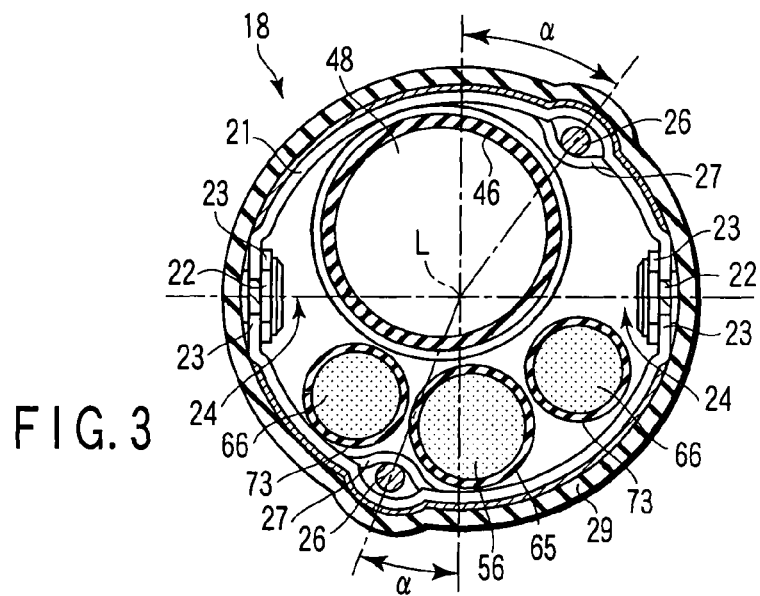
FIG. 3 is a cross-sectional view of the bending section of the endoscope of the same embodiment taken along line III-III of FIG. 2.

More specifically, lugs 23 are arranged on left and light sides of a front-end-side end face and a rear-end-side end face of each bending piece 21 so as to project toward each adjacent bending piece 21. The lugs 23 between each two adjacent bending pieces 21 overlap each other. As shown in FIG. 3, a shaft member 22 penetrates these overlapping lugs 23 and is riveted. A pivotal support portion 24 is formed in this manner. In the present embodiment, the pivotal support portion 24 is formed on right and left sides of the bending piece 21, so that the bending section 18 can be bent only in the vertical direction. If the pivotal support portion 24 is formed on upper and lower sides of the bending piece 21, moreover, the bending section 18 can be bent in the lateral direction.

Referring again to FIG. 2, guide rings 27 are attached individually to upper and lower sides of the bending piece 21, and control wires 26 are passed through the guide rings 27, individually. The respective distal end portions of the control wires 26 are inserted in the guide ring 27 of the bending piece 21 situated at the leading end and fixed to the bending piece 21 by brazing with solder or the like. Referring now to FIGS. 1 and 2, the control wires 26 are led out through the rear end portion of the bending section 18, passed through a guide sheath in the flexible tube section 17, and introduced into the hand control section 11. The rear end portions of the control wires 26 are coupled to a bending operation drive mechanism (not shown) in the hand control section 11. This bending operation drive mechanism pushes and pulls the control wires 26 as the bending operation lever 14 is rocked. If the control wire 26 on the upper side is pulled, the bending section 18 is bent upward. If the control wire 26 on the lower side is pulled, the bending section 18 is bent downward.

Thus, the bending section 18 can be bent only in the vertical direction by rocking the bending operation lever 14. In the present embodiment, a maximum upward bending angle of the bending section 18 is larger than a maximum downward bending angle. For example, the maximum upward bending angle is set to 210°, and the maximum downward bending angle to 120°. Thus, the tip forming portion 19 can be greatly raised upward.

The bending operation drive mechanism is provided with a stopper for limiting a maximum push/pull amount of the control wires 26, and the maximum bending angle of the bending section 18 is set by this stopper. Alternatively, the maximum bending angle may be set by forming an abutting portion for limiting the relative rocking angles of the adjacent bending pieces 21 on the front-end-side end face or the rear-end-side end face of the bending piece 21.

Figure 4:
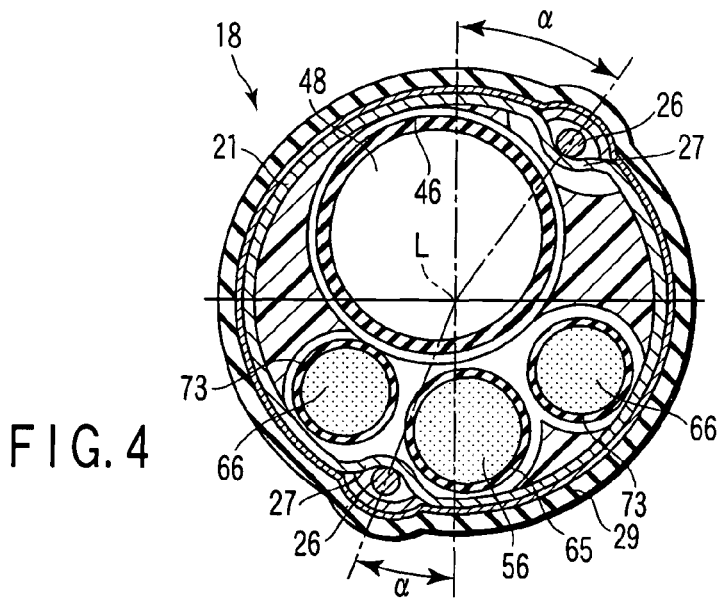
FIG. 4 is a cross-sectional view of the bending section of the endoscope of the same embodiment taken along line IV-IV of FIG. 2.

As shown in FIGS. 3 and 4, moreover, the guide rings 27 and the control wires 26 are not accurately located in positions right over and right under the central axis L, but are located with an angular shift α around the central axis L so as to give priority to the location of built-in members. Whereas they are located with this shift, the bending direction of the bending section 18 can be regarded as the vertical direction and thus there is no substantial inconvenience in use.

Referring again to FIG. 2, the outer peripheral surfaces of the bending pieces 21 of the bending section 18 are covered by a blade 28, and the outer peripheral surface of the blade 28 is covered by a skin 29. The distal end portion of the skin 29 is fitted on a first mounting-fit portion 81 (mentioned later) that is formed on the rear end portion of the tip forming portion 19.

Figure 5:
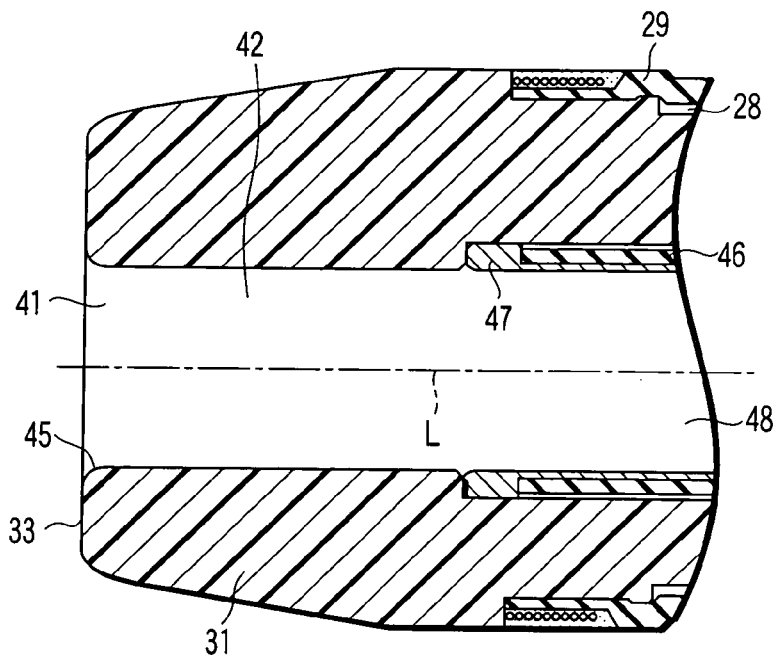
FIG. 5 is a longitudinal sectional view of the tip forming portion of the endoscope of the same embodiment taken along line V-V of FIG. 2.

The following is a description of a configuration of a channel 48 through which accessories are to be inserted. As shown in FIGS. 2 and 5, a channel bore 42 is formed in the tip forming portion 19. A distal opening of the channel bore 42 forms a channel port 41. A chamfer 45 is formed on the peripheral edge portion of the channel port 41 of the tip forming portion 19, covering the entire circumference. On the other hand, a channel tube 46 is connected to the rear end portion of the channel bore 42 through a connecting connecter 47. Referring to FIGS. 1 and 2, the channel tube 46 is introduced into the hand control section 11 through the bending section 18 and the flexible tube section 17 and connected to the channel connecter 15. Thus, the channel 48 is formed penetrating from the channel connecter 15 to the channel port 41.

The channel 48 can be used for air supply, water supply, etc., as well as for the insertion of the accessories. In performing air supply or water supply using the channel 48, an adapter of an air/water supply device (not shown) is connected to the channel connecter 15. Alternatively, air/water supply control buttons are provided on the hand control section 11 so that air supply and water supply can be performed by operating this air/water supply control buttons. Further, an alternative air/water supply channel may be provided in addition to the channel 48.

The following is a description of a configuration of an observation optical system for the observation of the subject's body. As shown in FIG. 2, this observation optical system has a first lens unit 52a on the distal end side and a second lens unit 53a on the rear end side. The first lens unit 52a has a first objective lens 52 formed of a lamination lens. The first objective lens 52 is assembled to a cylindrical inside lens frame 54. On the other hand, the second lens unit 53a has a second objective lens 53. The second objective lens 53 is fixed to the distal end portion of a connecter 57 that is fitted on the distal end portion of an image guide fiber 56. The outside diameter of the second objective lens 53 is substantially equal to the outside diameter of the connecter 57. A flexible tube 65 for protection is fitted on the image guide fiber 56 that extends from a rear end opening of the connecter 57. The image guide fiber 56 is introduced into the hand control section 11 through the bending section 18 and the flexible tube section 17 and connected to the eyepiece section 13 (see FIG. 1).

The first lens unit 52a and the distal end portion of the second lens unit 53a (the second objective lens 53 and the distal end side of the connecter 57) are successively inserted into a cylindrical outside lens frame 51 from the rear end side and fixed in a given position by adhesive bonding. This outside lens frame 51 is formed of a light-shielding resin or metal material. It is straight and has a substantially uniform inside diameter throughout its length. The first lens unit 52a and the distal end portion of the second lens unit 53a are movable in the direction of their optical axis before they are fixed to the outside lens frame 51 by adhesive bonding.

Further, the outside diameters of the first lens unit 52a and the distal end portion of the second lens unit 53a and the inside diameter of the outside lens frame 51 are set so that an allowance for an adhesive agent is defined between the outer peripheral surfaces of the first lens unit 52a and the distal end portion of the second lens unit 53a and the inner peripheral surface of the outside lens frame 51. Thus, these outside and inside diameters are set to generous dimensions such that the first lens unit 52a and the distal end portion of the second lens unit 53a can be inserted into given positions in the outside lens frame 51 with their outer peripheral surfaces coated with the adhesive agent and with the adhesive agent hardly scraped off.

A projection 58 for positioning the first lens unit 52a is formed on the distal end portion of the inner peripheral surface of the outside lens frame 51. The projection 58 has the shape of a claw that projects toward the central axis of the outside lens frame 51 and is formed covering the entire circumference of the inner peripheral surface of the outside lens frame 51. Alternatively, the projection 58 may be formed partially in the circumferential direction. The rear end face of the projection 58 is formed extending substantially at right angles to the central axis of the outside lens frame 51. When the first lens unit 52a is inserted into the outside lens frame 51 from its rear end side, the inside lens frame 54 of the first lens unit 52a is caused to abut against the rear end face of the projection 58, whereby the first lens unit 52a is positioned with respect to the outside lens frame 51. Thus, the projection 58 has a stopper function to define an insertion end position for the first lens unit 52a.

The length of the rear end face of the projection 58 in the radial direction of the central axis of the outside lens frame 51 is substantially equal to the thickness of the inside lens frame 54. Thus, the projection 58 can hardly intercept the field of view of the first objective lens 52 and spoil its optical function. Further, a taper portion is formed on the distal end side of the projection 58 so as to cover its entire circumference and that its inside diameter increases from the rear end side toward the distal end. The distal end portion of the taper portion is smoothly connected to the distal end face of the tip forming portion 19. A distal opening of the outside lens frame 51 forms an observation window 49. Thus, the distal end side of the projection 58 has a shape such that shading of an observation field can be minimized.

On the other hand, the outside lens frame 51 is inserted from the rear end portion into an observation hole 43, which penetrates the tip forming portion 19 from the rear end side to the distal end side, and fixed in a given position by adhesive bonding. The outside diameter of the outside lens frame 51 and the inside diameter of an inner wall that defines the observation hole 43 are set so that an allowance for the adhesive agent is defined between the outer peripheral surface of the outside lens frame 51 and the inner wall. Thus, these outside and inside diameters are set to generous dimensions such that the outside lens frame 51 can be inserted into a given position in the observation hole 43 with its outer peripheral surface coated with the adhesive agent and with the adhesive agent hardly scraped off.

The outside diameter of the outside lens frame 51 is larger in its rear-end-side region than in its distal-end-side region, and a step portion 62 is formed between the distal-end-side region and the rear-end-side region. On the other hand, the inner wall that defines the observation hole 43 has a shape such that the outside lens frame 51 can be fitted in it. More specifically, the inside diameter of the inner wall is larger in its rear-end-side region than in its distal-end-side region, and a step portion 64 is formed between the distal-end-side region and the rear-end-side region.

The outside lens frame 51 is inserted through a rear end opening of the observation hole 43 so that the step portion 62 of the outside lens frame 51 abuts against the step portion 64 of the inner wall, whereby the outside lens frame 51 is positioned with respect to the tip forming portion 19. Thus, these two step portions 62 and 64 have a stopper function to define an insertion end position for the outside lens frame 51. In this insertion end position, the outside lens frame 51 is fixed to the tip forming portion 19 by adhesive bonding.

Figure 6:
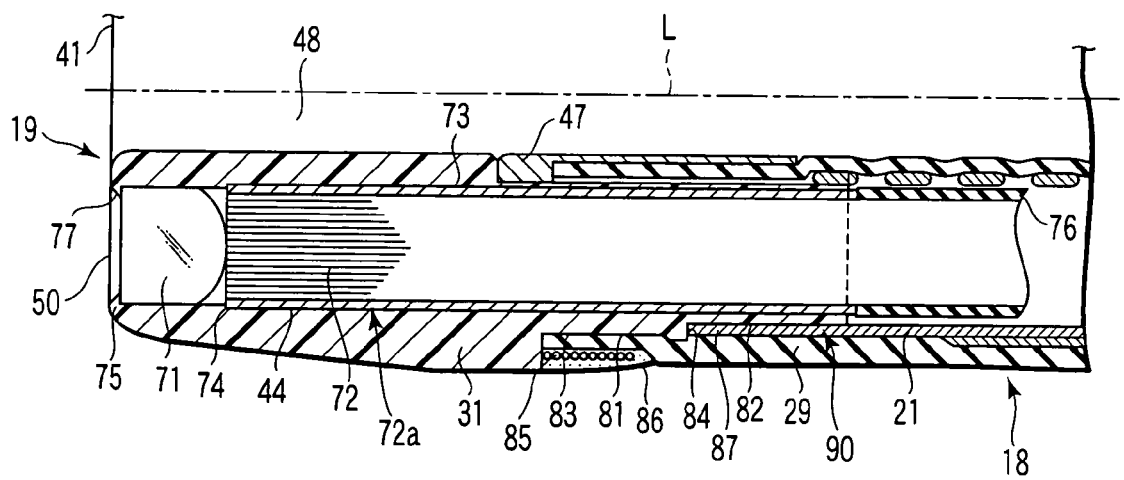
FIG. 6 is a longitudinal sectional view of the tip forming portion of the endoscope of the same embodiment taken along a section different from that of FIG. 2.
Figure 7:
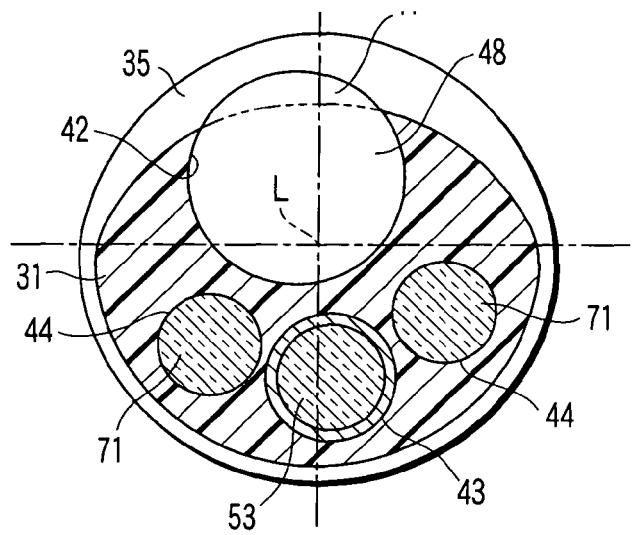
FIG. 7 is a cross-sectional view of the tip forming portion of the endoscope of the same embodiment taken along line VII-VII of FIG. 2.
Figure 8:
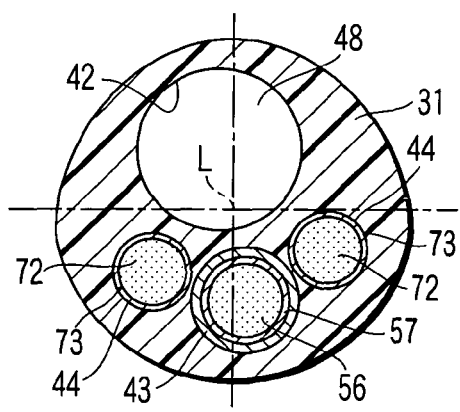
FIG. 8 is a cross-sectional view of the tip forming portion of the endoscope of the same embodiment taken along line VIII-VIII of FIG. 2.
Figure 9:
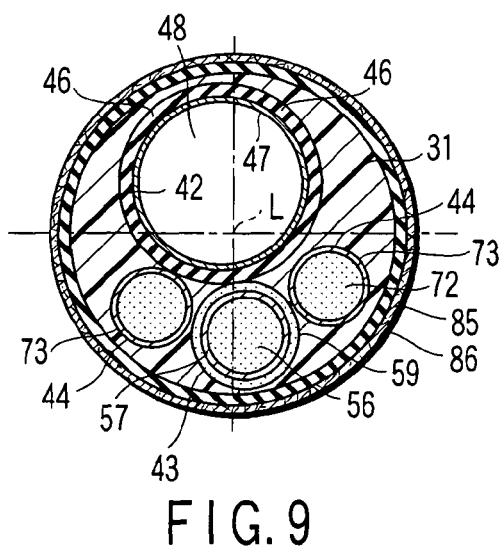
FIG. 9 is a cross-sectional view of the tip forming portion of the endoscope of the same embodiment taken along line IX-IX of FIG. 2.

The following is a description of a configuration of an illumination optical system for the illumination of the subject's body. As shown in FIG. 6, the illumination optical system has an illumination lens 71 on the distal end side and a fiber unit 72a on the rear end side. The illumination lens 71 serves as a cover glass, and a chamfer portion is formed on the peripheral edges of its distal end faces. On the other hand, the fiber unit 72a has a light guide fiber 72. A cylindrical distal connecter 73 is fitted on the distal end portion of the light guide fiber 72. A flexible tube 76 for protection is fitted on the light guide fiber 72 that extends from a rear end opening of the distal connecter 73. The light guide fiber 72 is introduced into the hand control section 11 through the bending section 18 and the flexible tube section 17 and further passed through the light guide cable 16 (see FIG. 1).

The illumination lens 71 and the distal end portion of the fiber unit 72a (the distal end side of the distal connecter 73) are successively inserted from the rear end side into an illumination hole 44, which penetrates the tip forming portion 19 from the rear end side to the distal end side, and fixed individually in given positions by adhesive bonding. The respective outside diameters of the illumination lens 71 and the distal end portion of the fiber unit 72a and the inside diameter of an inner wall that defines the illumination hole 44 are set so that an allowance for the adhesive agent is defined between the inner wall and the respective outer peripheral surfaces of the illumination lens 71 and the fiber unit 72a. Thus, these outside and inside diameters are set to generous dimensions such that the illumination lens 71 and the distal end portion of the fiber unit 72a can be inserted into given positions in the illumination hole 44 with their outer peripheral surfaces coated with the adhesive agent and with the adhesive agent hardly scraped off.

A projection 75 for positioning the illumination lens 71 is formed integrally on the distal end portion of the inner wall that defines the illumination hole 44. The projection 75 is formed covering the entire circumference of the inner wall. Alternatively, the projection 75 may be formed partially in the circumferential direction. The rear end face of the projection 75 is formed extending substantially at right angles to the central axis of the illumination hole 44. When the illumination lens 71 is inserted into the illumination hole 44 from its rear end side, a chamfer portion on the peripheral edge of the distal end face of the illumination lens 71 is caused to abut against the rear end face of the projection 75, whereby the illumination lens 71 is positioned with respect to the tip forming portion 19. Thus, the projection 75 has a stopper function to define an insertion end position for the illumination lens 71.

The length of the rear end face of the projection 75 in the radial direction of the central axis of the illumination hole 44 is substantially equal to the size of the chamfer portion of the illumination lens 71. Further, a taper portion is formed on the distal end side of the projection 75 so as to cover its entire circumference and that its inside diameter increases from the rear end side toward the distal end. The distal end portion of the taper portion is smoothly connected to the distal end face of the tip forming portion 19. A distal opening of the illumination hole 44 forms an illumination window 50. Since the projection 58 has this shape, the projection 75 can hardly spoil the optical function of the illumination optical system. Thus, although the projection 75 is a fine high-precision part, it can be easily fabricated by being molded together with a tip forming member 31 that forms the tip forming portion 19.

On the other hand, a step portion 74 for positioning the distal end portion of the fiber unit 72a is formed on the inner wall that defines the illumination hole 44. More specifically, the inside diameter of the inner wall is a little larger in its rear-end-side region than in its distal-end-side region in which the illumination lens 71 is housed. The step portion 74 is formed between the distal-end-side region and the rear-end-side region. When the distal end portion of the fiber unit 72a is inserted into the illumination hole 44 from its rear end side, the distal end portion of the distal connecter 73 of the fiber unit 72a is caused to abut against the step portion 74, whereby the fiber unit 72a is positioned with respect to the tip forming portion 19. Thus, the step portion 74 has a stopper function to define an insertion end position for the fiber unit 72a. In this insertion end position, the distal connecter 73 is fixed to the tip forming portion 19 by adhesive bonding.

The inside diameter of the distal-end-side region of the illumination hole 44 may be made larger than the outside diameter of the distal connecter 73 so that the distal connecter 73 can be inserted beyond the step portion 74 into the distal-end-side region.

As shown in FIGS. 7 to 10, the channel 48, observation hole 43, and illumination hole 44 are arranged side by side with one another and extends along the central axis L. The channel 48 is located in the upper center of a cross section perpendicular to the central axis L. Further, the observation hole 43 is located in the lower center, and a pair of illumination holes 44 is provided individually on the left and right sides of the observation hole 43.

Figure 11:
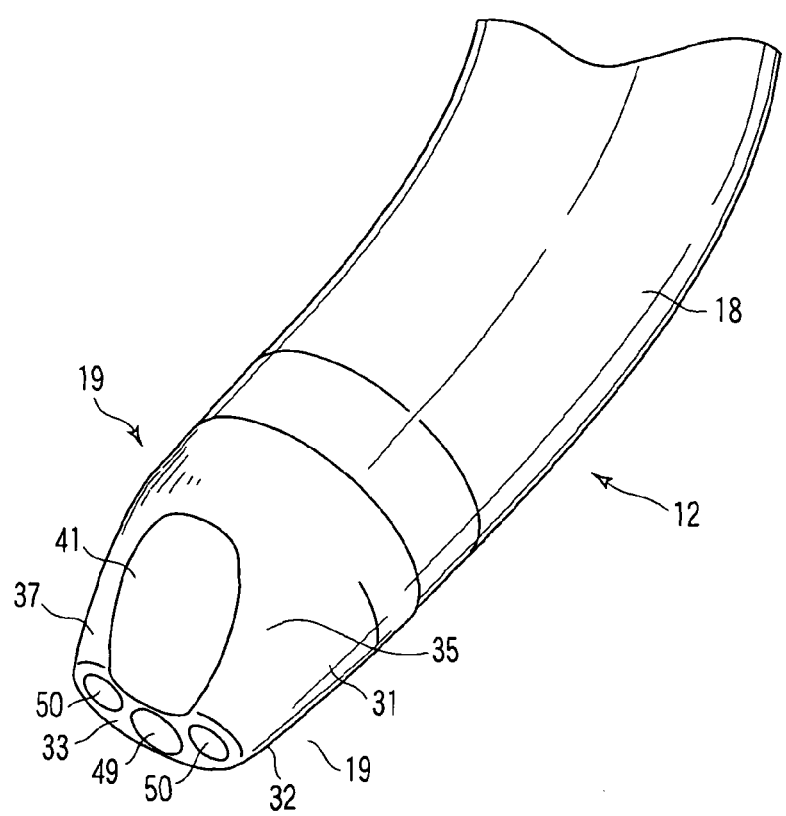
FIG. 11 is a perspective view showing the distal end portion of the endoscope of the same embodiment.

The following is a description of a configuration of the tip forming portion 19. As shown in FIG. 11, the tip forming portion 19 is formed with a paddle-shaped protrusion 32 that projects to the distal end side and is tapered toward the distal end. The protrusion 32 is located on the lower side of the tip forming portion 19. Formed on the upper side of the protrusion 32, moreover, is a slope portion 35 so that the tip forming portion 19 is tapered from the rear end side toward the distal end. The tip forming portion 19 can be greatly raised upward by the bending section 18 and the slope portion 35 is located on the raising direction side of the tip forming portion 19. The protrusion 32 and the slope portion 35 form a guide paddle portion 37. All of corner portions that are exposed to the outside of the tip forming portion 19 are rounded.

Figure 12:
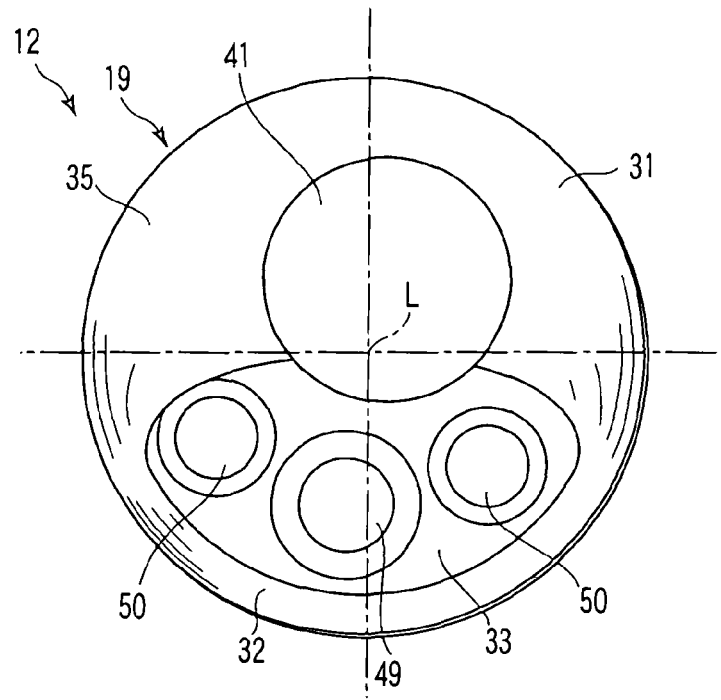
FIG. 12 is a front view showing an insertion section of the endoscope of the same embodiment.

The shape of the tip forming portion 19 will be described in detail with reference to FIGS. 12 to 14. As shown in FIG. 12, the protrusion 32 is located substantially in the lower-half region of an in-contour region of the tip forming portion 19, as viewed from the front. A distal end face 33 of the protrusion 32 is also located in the lower-half region. The distal end face 33 has a flat shape, long in the lateral direction and short in the vertical direction. In the present embodiment, it is substantially in the shape of an ellipse having its major axis in the lateral direction and its minor axis in the vertical direction. Further, the aforesaid observation window 49 of the observation optical system is located on the lower center of the distal end face 33. On the distal end face 33, moreover, the aforesaid pair of illumination windows 50 are located individually on the left and right sides of the observation window 49.

The distal end face 33 of the protrusion 32 is substantially elliptic, and the cross section of the proximal end portion of the tip forming portion 19, which is perpendicular to the central axis L of the insertion section 12, is substantially circular. The outer peripheral surface of the tip forming portion 19, which extends from the peripheral edge portion of the distal end face 33 to the peripheral edge portion of the proximal end portion of the tip forming portion 19, is a smooth continuous curved surface without any sharp corners or acute indentations, of which the cross section that is perpendicular to the central axis L have a shape changing from substantially ellipse to substantially circle.

On the other hand, the slope portion 35 is located above the protrusion 32. The aforesaid channel port 41 is located in the slope portion 35. Further, the lower end portion of the channel port 41 reaches the central upper part of the protrusion 32.

When the tip forming portion 19 is viewed sideways, as shown in FIG. 13, the slope portion 35 is a slope that slantingly descends from the upper end portion on the rear end side toward the lower end portion on the distal end side or from the upper part of the tip forming portion 19 to the vicinity of the central axis L of the insertion section 12 and projects toward the distal end. Further, the central part of the slope portion 35 is slightly curved and depressed downward. Thus, the inclination of the slope portion 35 is gentler on the distal end side, that is, the slope portion 35 is in the form of a gentle hill. An angle θ of inclination of the slope portion 35 to the central axis L of the insertion section 12 is relatively large. For example, the inclination angle θ ranges from 20° to 70°. A slanting portion 34 is also formed on the underside of the protrusion 32. It inclines at a relatively small angle from the lower end portion on the rear end side toward the upper end portion at the distal end side.

When the tip forming portion 19 is viewed from above, as shown in FIG. 14, the slope portion 35 has a laterally wide shape that slightly narrows from the rear end side toward the distal end within the width of the proximal end portion of the tip forming portion 19.

The tip forming portion 19 constructed in this manner is formed of the tip forming member 31 shown in FIG. 15. The tip forming member 31 is a single component that is integrally molded from a resin. A connecting portion 90 for connecting the tip forming member 31 to the bending section 18 (see FIG. 11) is located on the rear end side of the tip forming member 31.

As shown in FIG. 16, the outside diameter of the connecting portion 90 is smaller than the outside diameter of the distal end side of the tip forming member 31. Further, the connecting portion 90 has the first mounting-fit portion 81 on the distal end side and a second mounting-fit portion 82 on the rear end side. A shallow circumferential groove 83 is formed on the outer peripheral surface of the first mounting-fit portion 81, covering the entire circumference.

The outside diameter of the second mounting-fit portion 82 is a little smaller than the outside diameter of the first mounting-fit portion 81. Thus, a step portion 84 is formed between the first mounting-fit portion 81 and the second mounting-fit portion 82. The second mounting-fit portion 82 is formed with an axial notch, which defines a piece-like portion 20. Alternatively, the second mounting-fit portion 82 may be shaped to be cylindrical without being formed with the notch. One or a plurality of retaining protuberances 88 are formed on the outer peripheral surface of the second mounting-fit portion 82 by being molded integrally with the tip forming member 31. Two retaining protuberances 88 are used in the present embodiment. These retaining protuberances 88 are raised like a round knob each.

As shown in FIG. 6, the second mounting-fit portion 82 of the connecting portion 90 is fitted in a cylindrical distal end part 87 of the leading bending piece 21 of the bending section 18. The tip forming member 31 is positioned in the axial direction with the distal end portion of the distal end part 87 caused to abut against the step portion 84 of the connecting portion 90. Further, the distal end portion of the skin 29 is fixed on the outer peripheral surface of the first mounting-fit portion 81. A thread 85 is wound on the outer peripheral surface of the distal end portion of the skin 29, and the wound thread 85 is bound with an adhesive agent 86.

Figure 10:
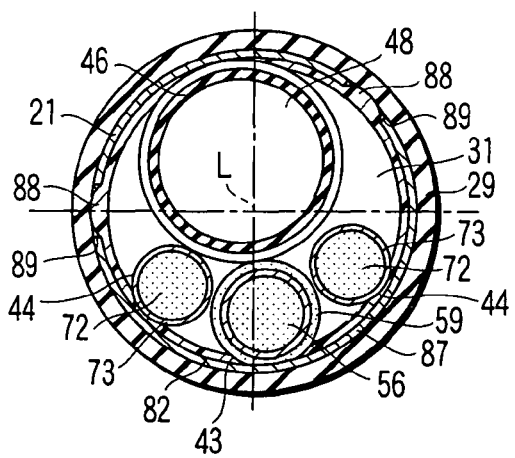
FIG. 10 is a cross-sectional view of the tip forming portion of the endoscope of the same embodiment taken along line X-X of FIG. 2.

As shown in FIG. 10, the retaining protuberances 88 of the second mounting-fit portion 82 are fitted individually into retaining holes 89 that are formed in the distal end part 87 of the leading bending piece 21. The height of the retaining protuberances 88 is set within the depth of the retaining holes 89. Alternatively, the height of the retaining protuberances 88 may be set to a value not smaller than the depth of the retaining holes 89 such that they don't push up the skin 29.

If the retaining protuberances 88 and the retaining holes 89 are plural in number, the retaining protuberances 88 and the retaining holes 89 should preferably be located in positions that are asymmetric with respect to the central axis L. In the present embodiment, the two retaining protuberances 88 and the two retaining holes 89 are located individually in an upper position and a side position (one of right position and left position). Thus, the position of connection of the tip forming member 31 to the bending section 18 (see FIG. 11) around the central axis L is restricted to one in number.

The following is a description of assembly processes for the endoscope 10 of the present embodiment. Assembly processes for the observation optical system will be described first. The first lens unit 52*a* is formed in a first process, among the assembly processes for the observation optical system. More specifically, the first objective lens 52 is assembled to the inside lens frame 54.

In a second process, the first lens unit 52*a* is assembled to the outside lens frame 51. More specifically, the adhesive agent is applied to the outer peripheral surface of the inside lens frame 54, and the inside lens frame 54 is inserted into the outside lens frame 51 through is rear end opening. Then, the inside lens frame 54 is pushed forward in the outside lens frame 51 by means of using a suitable tool. In consequence, the distal end portion of the inside lens frame 54 is caused to abut against the rear end face of the projection 58, whereupon the movement of the inside lens frame 54 toward the distal end is stopped, and the inside lens frame 54 is positioned with respect to the outside lens frame 51. In this position, the adhesive agent is cured so that the inside lens frame 54 is fixed to the outside lens frame 51.

In a third process, the second lens unit 53*a* is assembled to the outside lens frame 51. More specifically, the adhesive agent is applied to the respective outer peripheral surfaces of the second objective lens 53 and the connecter 57, and the second objective lens 53 and the connecter 57 are inserted into the outside lens frame 51 through its rear end opening. Then, the second objective lens 53 and the connecter 57 are pushed forward with respect to the outside lens frame 51. When the second objective lens 53 approaches the first objective lens 52, the eyepiece section 13 is looked in, and the second objective lens 53 is positioned with respect to the outside lens frame 51 so that the focusing is performed. In this position, the adhesive agent is cured to fix the second objective lens 53 and the connecter 57 to the outside lens frame 51.

In the first to third processes described above, the first objective lens 52, second objective lens 53, and image guide fiber 56 are assembled to the outside lens frame 51 and unitized, and besides, optical adjustment between them is completed.

In a fourth process, the outside lens frame 51 is assembled to the tip forming member 31. More specifically, the adhesive agent is applied to the outer peripheral surface of the outside lens frame 51, and the outside lens frame 51 is inserted into the observation hole 43 of the tip forming member 31 through its rear end opening. Then, the outside lens frame 51 is pushed forward in the observation hole 43. In consequence, the step portion 62 of the outside lens frame 51 is caused to abut against the step portion 64 in the observation hole 43, whereupon the movement of the outside lens frame 51 toward the distal end is stopped, and the outside lens frame 51 is positioned with respect to the tip forming member 31. In this position, the adhesive agent is cured so that the outside lens frame 51 is fixed to the tip forming member 31. Further, an adhesive agent 59 (see FIG. 2) is filled into a space between the outer peripheral surface of the connecter 57, which projects from the rear end opening of the outside lens frame 51, and the inner wall of the observation hole 43, and the adhesive agent 59 is cured to fix the connecter 57 to the tip forming member 31.

In the assembly processes for the observation optical system described above, the optical adjustment between the first objective lens 52, second objective lens 53, and image guide fiber 56 is performed before they are assembled to the tip forming member 31 of the endoscope 10. Therefore, operation for the optical adjustment between these members is simple. When compared with a case where the optical adjustment is performed as these members are assembled to the endoscope 10, moreover, reduction of the yield of the endoscope 10 can be prevented, so that the productivity is improved.

In assembling the outside lens frame 51, assembled with these members, to the tip forming member 31, furthermore, the outside lens frame 51 can be positioned with respect to the tip forming member 31 and fixed to it by only inserting the tip forming member 31, having the adhesive agent spread on its outer peripheral surface, into the observation hole 43 through its rear end opening. Thus, assembling the outside lens frame 51 is so easy that the assemblability is improved. Further, the assembling does not require use of any additional components, so that the number of components is reduced.

The following is a description of assembly processes for the illumination optical system. In a first process, the illumination lens 71 is assembled to the tip forming member 31. More specifically, the adhesive agent is applied to the outer peripheral surface of the illumination lens 71, and the illumination lens 71 is inserted into the illumination hole 44 through its rear end opening. Then, the illumination lens 71 is pushed forward by using a tool for insertion or the like. Since the inside diameter of a rear-end-side region of the illumination hole 44 that ranges from the rear end opening to the step portion 74 is relatively large, the illumination lens 71 can be easily pushed forward, and the adhesive agent spread on the outer peripheral surface of the illumination lens 71 can hardly be scraped off in the middle.

Then, the illumination lens 71 is inserted beyond the step portion 74 into the distal-end-side region and caused to abut against the projection 75, whereupon the movement of the illumination lens 71 to the distal end side is stopped, and the illumination lens 71 is positioned with respect to the tip forming member 31. In this position, the adhesive agent is cured to fix the illumination lens 71 to the tip forming member 31.

In a second process, the fiber unit 72*a* is assembled to the tip forming member 31. More specifically, the adhesive agent is applied to the outer peripheral surface of the distal connecter 73 of the light guide fiber 72, and the fiber unit 72*a* is inserted into the illumination hole 44 through its rear end opening. Then, the fiber unit 72*a* is pushed forward in the illumination hole 44. In consequence, the distal end portion of the distal connecter 73 is caused to abut against the step portion 74 of the illumination hole 44, whereupon the movement of the fiber unit 72*a* toward the distal end is stopped, and the light guide fiber 72 is positioned with respect to the tip forming member 31. In this position, the adhesive agent is cured to fix the fiber unit 72*a* to the tip forming member 31.

Alternatively, the light guide fiber 72 may be positioned after the illumination lens 71 is positioned. In this case, the adhesive agent on the illumination lens 71 and the adhesive agent on the fiber unit 72*a* are cured simultaneously, thereafter.

In the assembly processes for the illumination optical system described above, the illumination lens 71 is inserted into the illumination hole 44 through its rear end opening and caused to abut against the projection 75 so that it is positioned with respect to the tip forming member 31 and fixed. Thus, the illumination lens 71 can be accurately positioned with respect to the front-rear direction and securely fixed with ease, so that the assemblability is improved.

In the present embodiment, the outside lens frame 51 is assembled to the tip forming member 31 after the observation optical system is assembled to the outside lens frame 51. As for the illumination optical system, it is assembled directly to the tip forming member 31. Alternatively, the observation optical system, like the illumination optical system, may be assembled directly to the tip forming member 31.

The following is a description of assembly processes for the tip forming member 31. In assembling the tip forming member 31 to the distal end portion of the bending section 18, the tip forming member 31 is first positioned in the front-rear direction with respect to the bending section 18. More specifically, the second mounting-fit portion 82 of the tip forming member 31 is fitted into the cylindrical distal end part 87 of the leading bending piece 21. Then, the distal end portion of the distal end part 87 is caused to abut against the step portion 84 of the tip forming member 31, whereupon the movement of the tip forming member 31 toward the rear end is stopped, and the tip forming member 31 is positioned in the front-rear direction with respect to the bending section 18.

Here the tip forming member 31 is formed of a resin that is relatively flexible, the height of the retaining protuberances 88, which is substantially equal to the thickness of the distal end part 87 of the bending piece 21, is relatively small, and the retaining protuberances 88 are raised like a round knob each. Besides, the second mounting-fit portion 82 is formed as the piece-like portion 20. In fitting the second mounting-fit portion 82 into the distal end part 87, therefore, the second mounting-fit portion 82 can be pushed in smoothly by the agency of a slight deformation of the second mounting-fit portion 82 and slight elastic escape action by the piece-like portion 20.

Then, the tip forming member 31 is positioned around the central axis L with respect to the bending section 18. More specifically, the second mounting-fit portion 82 is fitted into the distal end part 87 in anticipation of their positional relationship, so that the retaining protuberances 88 may possibly be fitted directly into the retaining holes 89 of the distal end part 87. However, they cannot be fitted if the position around the central axis L is shifted. In this case, the bending pieces 21 or the tip forming member 31 is relatively rotated around the central axis L to search for engagement positions between the retaining protuberances 88 and the retaining holes 89. If the retaining protuberances 88 and the retaining holes 89 are aligned with one another, the retaining protuberances 88 are automatically fitted into the retaining holes 89, whereupon they engage one another. The completion of this engagement can be easily recognized by a feeling or sound with which the retaining protuberances 88 are fitted into the retaining holes 89. By this engagement, the tip forming member 31 is positioned around the central axis L with respect to the bending section 18. In this manner, the tip forming member 31 can be positioned in a given direction with respect to the bending section 18. In the present embodiment, the slope portion 35 of the tip forming member 31 is located above the central axis L or in one bending direction of the bending section 18. With the engagement between the retaining protuberances 88 and the retaining holes 89, moreover, the tip forming member 31 can be securely held with respect to the leading bending piece 21, and the subsequent operation can be performed with ease.

Thereafter, the second mounting-fit portion 82 and the distal end part 87 are bonded together, and the tip forming member 31 and the leading bending piece 21 are fixed to each other. Further, the distal end part of the skin 29 that extends from the bending section 18 is fitted on the second mounting-fit portion 82, the thread 85 is wound around the distal end part of the skin 29, and the wound thread 85 is bound with the adhesive agent 86.

In the assembly process for the tip forming member 31 described above, the tip forming member 31 can be positioned simply, easily, and accurately with respect to the bending section 18. Therefore, the slope portion 35 of the tip forming member 31 can be accurately fixed to the bending section 18 in a given direction, and the assembly accuracy can be improved. Besides, this positioning mechanism includes a small number of components.

Figure 21:
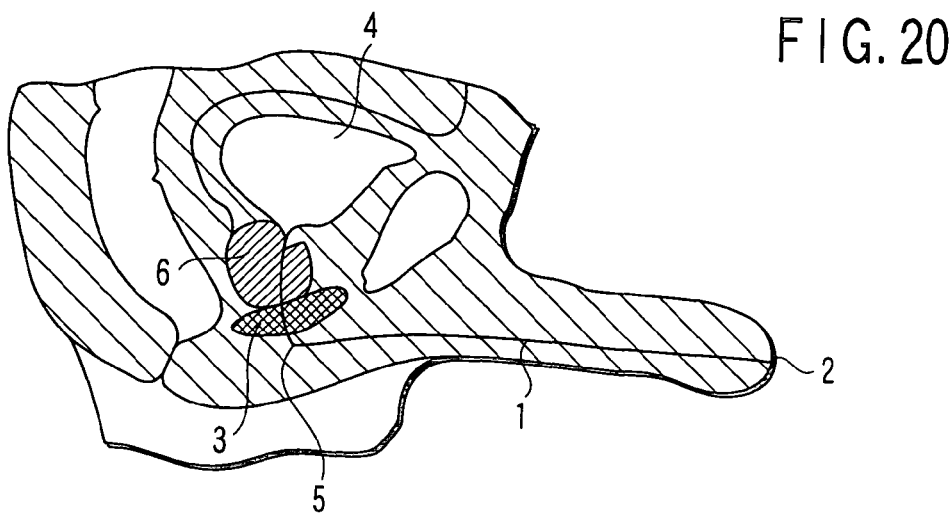
FIG. 21 is an anatomical view showing the urethra of a male person.

The following is a description of operation for inserting the endoscope 10 of the present embodiment into a urethra 1. In inserting the insertion section 12 of the endoscope 10 into the urethra 1 shown in FIG. 21, the distal end of the insertion section 12 is inserted into an external urethral orifice 2, and the insertion section 12 is pushed forward in the occluded urethra 1. Anatomically, the urethra 1 is loosely occluded and formed straight to its region just short of a urethral sphincter 3, so that the insertion section 12 can be inserted relatively easily into it by being pushed in straight.

However, the urethra 1 is sharply bent upward at a bent part 5 that is located just short of the urethral sphincter 3. In the vicinity of the bent part 5, moreover, the urethra 1 is occluded by a throttle function of the urethral sphincter 3 to close up the urethra 1, so that the urethra 1 is narrowed. In the case of a patient whose prostate 6 is starting to hypertrophy, in particular, the urethra 1 near that region is further narrowed. Thus, a technique to pass the tool through the bent part 5 is the hardest performance and easily inflicts pain on the patient.

Figure 17:
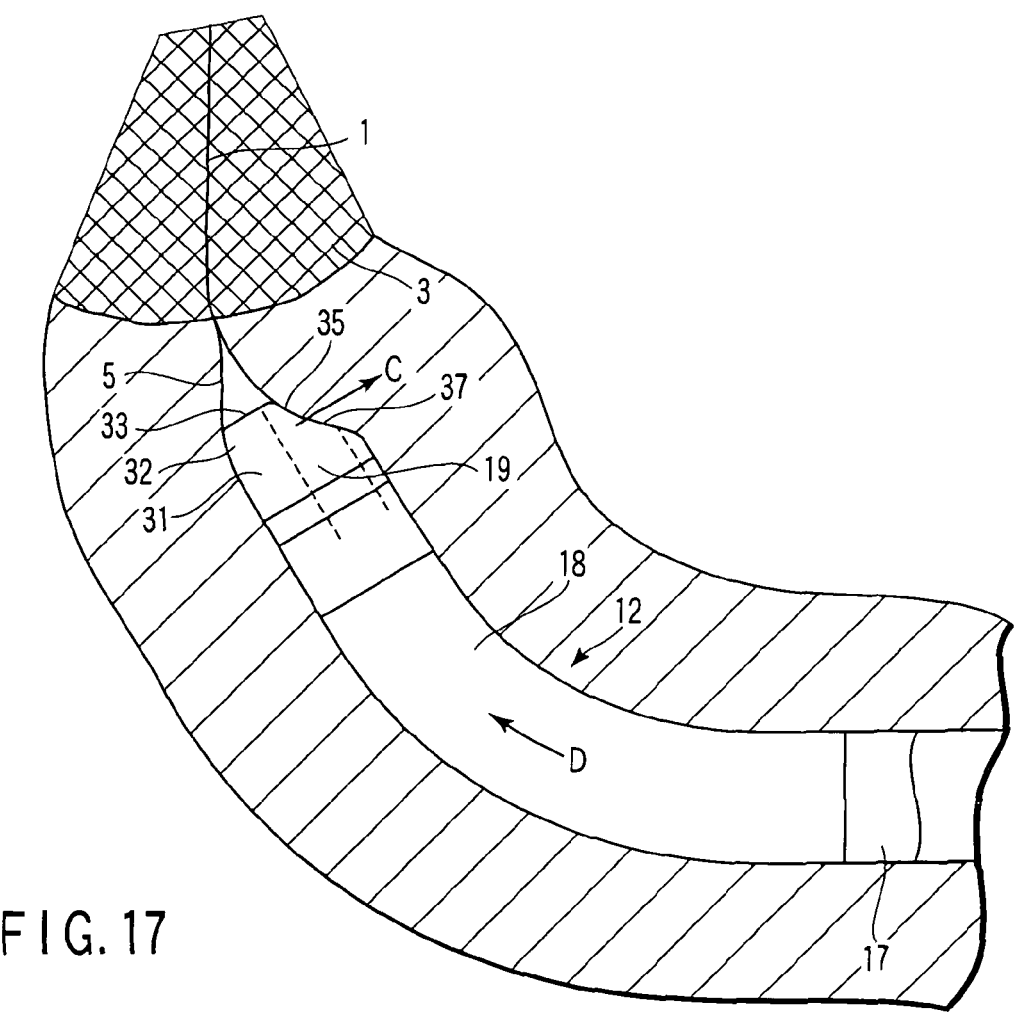
FIG. 17 is a view for illustrating the way in which the endoscope of the same embodiment is inserted into a urethra.

The endoscope 10 of the present embodiment is operated in the following manner to insert and pass the tip forming portion 19 of the insertion section 12 through the bent part 5. More specifically, in inserting the tip forming portion 19 into the bent part 5 that is bent upward and occluded, as shown in FIG. 17, the bending section 18 of the insertion section 12 is curved upward (see arrow C of FIG. 17). In consequence, the tip forming portion 19 is raised upward by the distal end portion of the bending section 18. Thereupon, the slope portion 35 of the tip forming portion 19 presses the inner wall (urethral wall) of the urethra 1, and the guide paddle portion 37 behaves as the so-called paddle to push up the urinary tract wall of the urethra 1. By this push-up action, the occlusion of the urethra 1 is eased to secure the insertion path of the tip forming portion 19. By simultaneously performing the bending operation for the bending section 18 and the push-in operation (see arrow D of FIG. 17) for the insertion section 12, moreover, the insertion path can be secured, and the tip forming portion 19 is guided to slide into the depth by the protrusion 32. Thus, the tip forming portion 19 can be inserted smoothly. Further, the upwardly curved bending section 18 follows the tip forming portion 19 and is inserted into the upwardly bent part 5. In this manner, the insertion section 12 easily passes through the occluded bent part 5.

The outer peripheral surface of the tip forming portion 19 is a smooth curved surface that changes from the substantially elliptic distal end face 33 to a substantially circular rear-end-side cross section that is perpendicular to the axial direction. In inserting the tip forming portion 19 into the urethra 1, therefore, the tip forming portion 19 is smoothly moved along the inner wall of the urethra 1, covering the overall length of the urethra 1. Further, the distal end face 33 is formed so as to be situated on the lower side of the tip forming portion 19, as viewed from the front, or in one bending direction of the bending section 18. In inserting the tip forming portion 19 into the constricted urethra 1 that, like the urethra 1 suffering prostatomegaly, has a substantially waterdrop-like cross-sectional shape in the vertical direction, therefore, the distal end face 33 first passes through a widely opening part on the lower side of the urethra. Thereafter, the tip forming portion 19 passes through a narrowed part of the prostate or the like in a manner such that its outer peripheral surface gently spreads the narrowed part.

As the insertion section 12 is inserted into the urethra 1 with its slope portion 35 pushing up the inner wall of the urethra 1, the state of the inner wall of the urethra 1 is observed through the observation window 49 and illumination windows 50 in the distal end face 33 of the protrusion 32, whereby a lesion, bleeding, etc., are checked for presence.

In the insertion operation of the endoscope 10 of the present embodiment described above, the guide paddle portion 37 behaves as the so-called paddle as the bending section 18 bends, whereby the inner wall of the urethra 1 is pushed up to secure the insertion path of the tip forming portion 19. By simultaneously performing the bending operation for the bending section 18 and the push-in operation for the insertion section 12, moreover, the tip forming portion 19 is guided into the depth by the protrusion 32. Thus, the ability of the insertion section 12 to be inserted into the lumen of the subject's body that has a bent part or an occluded part is enhanced, so that pain inflicted on the patient can be minimized.

Further, the outer peripheral surface of the tip forming portion 19 is the smooth curved surface that changes from the substantially elliptic distal end face 33 to the substantially circular rear-end-side cross section that is perpendicular to the axial direction. In inserting the tip forming portion 19 into the lumen of the subject's body, therefore, it can be smoothly inserted along the inner wall. In passing the tip forming portion 19 through a bent constricted part or the like near the urethral sphincter 3 of the urethra 1 of a male person, in particular the tip forming portion 19 can be smoothly inserted with it swung by bending operation and its outer peripheral surface moving along the inner wall of the urethra 1. Thus, the ability of the insertion is more enhanced.

Besides, the distal end face 33 is formed so as to be situated on the lower side of the tip forming portion 19, as viewed from the front. In inserting the tip forming portion 19 into the lumen that has a substantially teardrop-like cross-sectional shape in the vertical direction, therefore, the distal end face 33 first passes through the widely opening lower part. Thereafter, the tip forming portion 19 passes through the lumen in a manner such that its outer peripheral surface gently spreads the lumen. Thus, pain inflicted on the patient can be minimized.

Figure 18:
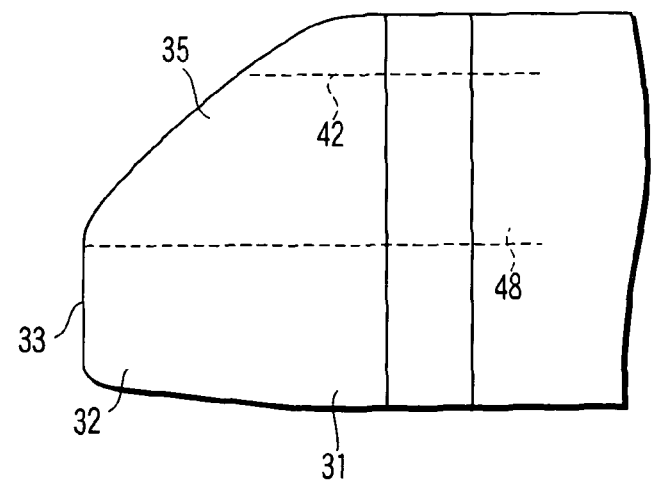
FIG. 18 is a side view showing a tip forming portion of an endoscope according to a first modification of the same embodiment.

According to the present invention, moreover, the endoscope 10 may be modified in the following manner. In a modification shown in FIG. 18, the slope portion 35 of the paddle-shaped protrusion 32 of the tip forming portion 19 slightly swells outward.

Figure 19:
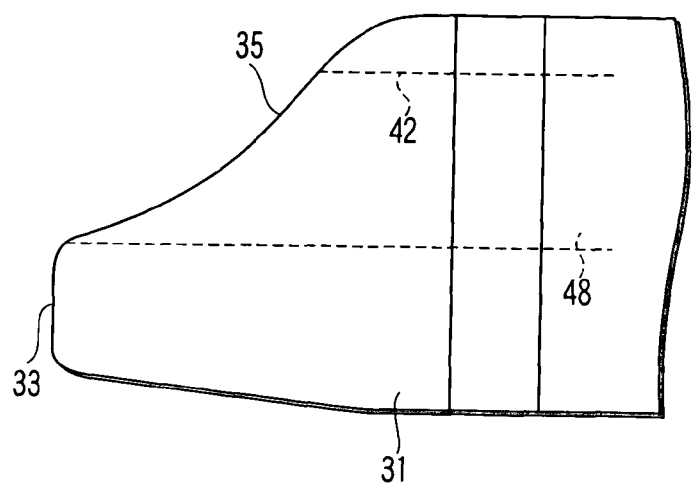
FIG. 19 is a side view showing a tip forming portion of an endoscope according to a second modification of the same embodiment.

In a modification shown in FIG. 19, the projection length of the paddle-shaped protrusion 32 of the tip forming portion 19 is increased. Correspondingly, the slope portion 35 of the paddle-shaped protrusion 32 also extends gently toward the distal end. The same functions and effects as aforesaid can be also obtained in this case.

Figure 20:
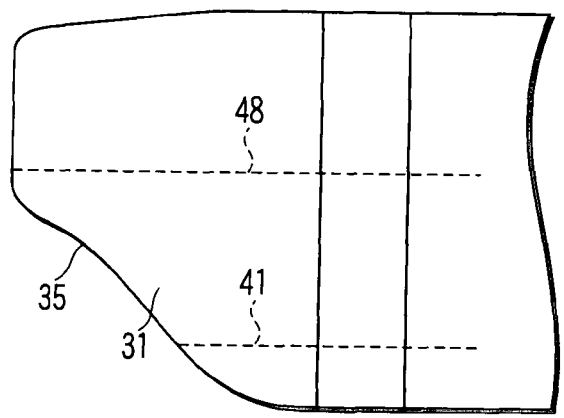
FIG. 20 is a side view showing a tip forming portion of an endoscope according to a third modification of the same embodiment.

In a modification shown in FIG. 20, the paddle-shaped protrusion 32 of the tip forming portion 19 is located on the lower side, and the lower surface of the protrusion 32 forms the slope portion 35. In this case, the tip forming portion 19 can be easily passed through a downwardly bent lumen, and the same functions and effects as aforesaid can be obtained. Further, the slope portions 35 may be formed individually on the upper and lower sides of the protrusion 32.

Furthermore, the observation window 49 and the illumination windows 50 in the distal end face 33 of the protrusion 32 of the tip forming portion 19, especially the illumination windows 50, may be located on the slope portion 35. Alternatively, the illumination windows 50 may be located individually on both the distal end face 33 and the slope portion 35. Further, the slope portion 35 of the tip forming portion 19 may be formed without having any of the observation window 49, illumination windows 50, and channel port 41.

The present invention is not limited directly to the embodiments described above, and in carrying out the invention, its components may be embodied in modified forms without departing from the spirit of the invention. Further, various inventions may be made by suitably combining a plurality of components described in connection with the foregoing embodiments. For example, some of the components according to the foregoing embodiments may be omitted. Furthermore, components according to different embodiments may be combined as required.

The following is a description of preferred aspect of the embodiment of the present invention.

(Aspect 1) In an endoscope for observing a subject's body, the endoscope comprises a tip portion provided on the distal end of a bending section of an insertion section to be inserted into a lumen of the subject's body, a paddle-shaped protrusion projecting forward in the tip portion, and a slope portion which is formed of the surface of that part of the paddle-shaped protrusion which extends from the distal end of the paddle-shaped protrusion to the proximal portion of the tip portion on the side of the direction in which the bending section bends and abuts against an inner wall of the lumen.

(Aspect 2) In an endoscope for observing a subject's body, the endoscope comprises an insertion section configured to be inserted into the subject's body, a bending section provided on the insertion section and bendable in a given direction, and a slope portion provided on the given-direction side of the tip portion of the insertion section.

(Aspect 3) In an endoscope for observing a subject's body, the endoscope comprises an insertion section configured to be inserted into the subject's body, a bending section provided on the insertion section and bendable in a given direction, and a slope portion provided on the given-direction side of the tip portion of the insertion section and configured to press the subject's body.

(Aspect 4) In an endoscope for observing a subject's body, the endoscope comprises an insertion section configured to be inserted into the subject's body, a bending section which forms a part of the insertion section and is bendable in a given direction in response to operation of a control section, a frame body having a shape such as to be connectable to a tip portion of the insertion section and formed with a slope portion tapered from the proximal end side toward the distal end side, and a fixing portion which fixes the frame body to the tip portion of the insertion section so that the slope portion is located on the given direction side.

(Aspect 5) In an endoscope for observing a subject's body, the endoscope comprises an insertion section configured to be inserted into the subject's body, a frame body provided on a tip portion of the insertion section and formed, in a given direction, with a slope portion tapered from the proximal end side toward the distal end side, a bending section which forms the insertion section and is bendable, and control means which controls the bending section to bend to the given direction side.

What is claimed is:

1. A flexible endoscope comprising an insertion section,
wherein the insertion section extends in an axial direction, includes a bending section configured to be bendable in a first and a second bending orientation opposite to each other, of a bending direction substantially orthogonal to the axial direction and a tip forming portion provided at a distal end portion of the bending section, and is configured to be inserted into a lumen from the tip forming portion,
the tip forming portion includes a paddle-shaped protrusion,
the paddle-shaped protrusion is located close to a first bending orientation side in the tip forming portion, protrudes toward a distal end side so as to taper within the width of a proximal end portion of the tip forming portion, is formed to be wide in a lateral direction substantially orthogonal to the axial direction and the bending direction, and includes a slope portion and a distal end face,
the slope portion is wide in the lateral direction, located on a second bending orientation side in the paddle-shaped protrusion, formed such that a distal end side of the slope portion is located close to the first bending orientation side, a proximal end side of the slope portion is located close to the second bending orientation side and a distal end of the slope portion is located on a distal end of the whole tip forming portion with respect to the axial direction, and the slope portion is provided with a channel port and
the distal end face of the paddle-shaped protrusion forms a distal end face of the whole tip forming portion, is protruded, and includes a first part thereof, wherein the whole of the first part is substantially orthogonal to the axial direction and has a substantially elliptical shape whose minor axis extends in the bending direction and whose major axis extends in the lateral direction, and the first part is provided with an illumination window and an observation window.

2. The endoscope according to claim 1, wherein a peripheral surface of the tip forming portion except for the slope portion tapers from a proximal end side to a distal end side.

3. The endoscope according to claim 1, wherein the slope portion includes a depressed slope.

4. The endoscope according to claim 1, wherein the tip forming portion including the paddle-shaped protrusion is molded from a resin as one part.

* * * * *